United States Patent
Kandeel et al.

(10) Patent No.: US 12,150,922 B1
(45) Date of Patent: Nov. 26, 2024

(54) METHODS OF INHIBITING CYCLOOXYGENASE (COX) USING TOLTERODINE

(71) Applicant: KING FAISAL UNIVERSITY, Al Hasa (SA)

(72) Inventors: Mahmoud Kandeel, Al-Ahsa (SA); Abdulla Altaher, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/533,619

(22) Filed: Dec. 8, 2023

(51) Int. Cl.
*A61K 31/137* (2006.01)

(52) U.S. Cl.
CPC .................. *A61K 31/137* (2013.01)

(58) Field of Classification Search
CPC .................................................. A61K 31/137
See application file for complete search history.

(56) References Cited

U.S. PATENT DOCUMENTS

| | | | |
|---|---|---|---|
| 7,005,449 B2 * | 2/2006 | Hawley | A61P 11/00 514/555 |
| 2006/0004076 A1 | 1/2006 | Patel et al. | |
| 2023/0285405 A1 | 9/2023 | Tay et al. | |

FOREIGN PATENT DOCUMENTS

EP   3569228 A1   11/2019

OTHER PUBLICATIONS

Smith et al., "Pharmacological analysis of cyclooxygenase-1 in inflammation", Proceedings of the National Academy of Sciences of the United States of America, vol. 95, No. 22, pp. 13313-13318 (1998).*
Johnston, et al. "Repurposing of approved drugs from the human pharmacopoeia to target Wolbachia endosymbionts of onchocerciasis and lymphatic filariasis", International Journal for Parasitology: Drugs and Drug Resistance, vol. 4, Issue 3, 2014, pp. 278-286.
Macraild, et al. "Systematic Down-Selection of Repurposed Drug Candidates for COVID-19". Int J Mol Sci. Oct. 6, 2022;23(19):11851.

* cited by examiner

*Primary Examiner* — Kevin E Weddington
(74) *Attorney, Agent, or Firm* — Nath, Goldberg & Meyer; Joshua B. Goldberg

(57) ABSTRACT

A method of inhibiting cyclooxygenase (COX) enzyme activity in a patient including administering to a patient in need thereof a therapeutically effective amount of tolterodine.

10 Claims, No Drawings

METHODS OF INHIBITING CYCLOOXYGENASE (COX) USING TOLTERODINE

BACKGROUND

1. Field

The present disclosure provides a method of inhibiting COX-1 and COX-2, an enzyme responsible for inflammation and pain, by administering to a patient a therapeutically effective amount of tolterodine. Tolterodine is useful as a therapeutic agent for reducing pain and inflammation.

2. Description of the Related Art

Non-steroidal anti-inflammatory drugs (NSAIDs) have been therapeutically used in the medication of rheumatic arthritis and also in the treatment of various inflammatory disorders. Due to their gastrointestinal side effects, they are often used in limited numbers.

Cyclooxygenase-2 (COX-2) enzyme has been implicated in various physiological and pathological roles, notably in cancer development and progression. It is overexpressed in several cancer types and contributes to tumor growth by promoting angiogenesis, cell proliferation, and inhibiting apoptosis.

In the treatment of inflammatory episodes, NSAIDs constitute the gold standard. NSAIDs, by definition, reduce inflammation and relieve pain, but are not related to steroids (which also reduce inflammation). NSAIDs block the production of certain body chemicals associated with inflammation, thereby treating pain, fever, and other inflammatory effects on the body. One of the most common NSAIDs is aspirin.

Inflammation is associated with redness, pain, and swelling. Inflammation may be acute, or it may be chronic. Some diseases are associated with chronic inflammation—such as arthritis and rheumatoid arthritis, diabetes, asthma, autoimmune diseases, Alzheimer's, and cardiovascular disease, among many others. Prostaglandins act as mediators of acute inflammation and may also play a part in chronic inflammation.

Certain NSAIDs reduce the production of prostaglandins, which play a key role in generating the inflammatory response. Specifically, such NSAIDs block cyclooxygenase (COX) enzymes, which are involved in formation of prostaglandins. Inhibition of COX enzymes impairs or inhibits prostaglandin synthesis, resulting in reduction of inflammation and associated effects of inflammation.

In this context, cyclooxygenases 1 and 2 (COX-1 and COX-2) and arachidonate 5-lipooxygenase (5-lox) play key roles in the production and regulation of inflammation. COX-1 is expressed predominantly in the gastrointestinal tract, while COX-2 is predominantly produced at sites of inflammation. The stomach lining and renal functions are protected by certain prostaglandins produced by COX-1. COX-2 is activated in response to inflammation and is, therefore, inducible in nature. The enzyme 5-lox is involved in transforming essential fatty acid substrates into leukotrienes (as well as other biologically active products). Leukotrienes (LTs) are the first class of mediators that contribute to the inflammatory process. LTs play a significant part in the inflammatory process overall.

Prostaglandin E2 (PGE2) and prostaglandin I2 (PGI2, or prostacyclin) increase blood flow in inflamed areas by their potent vasodilator action. PGI2 is responsible for platelet aggregation and vascular endothelium inhibition. The vasodilation effect of Prostaglandin E2 and Prostacyclin I2 acts to protect the gastric mucosa by increasing the secretion of mucus and preventing the increase of acidity and pepsin content in the stomach. In the kidneys, PGE and PGI play a role in increasing the blood flow and regulation of the glomerular filtration rate.

Non-steroidal anti-inflammatory drugs are the gold standard in treating inflammatory episodes due to their ability to block the arachidonic acid pathways. Certain NSAIDs act by selective or non-selective inhibition of COX-1 and COX-2 enzymes. In addition to lowering inflammation, however, currently available non-selective medicines inhibit platelet aggregation. Additionally, the existing non-selective medications raise the risk of stomach ulcers and bleeding such as indomethacin. Some medications used to treat pain and inflammation, such as Celecoxib, can also cause heart-related side effects Accordingly, development of new NSAIDs that result in reduced frequency and severity of negative side effects is desired.

SUMMARY

The present subject matter relates to methods of inhibiting cyclooxygenase, an enzyme critical in the production of prostaglandins. The method includes administration of tolterodine as a NSAID compound. NSAID compounds are well-known generally for their effectiveness in reducing inflammation, fever, and pain, primarily by inhibiting the cyclooxygenase (COX) enzymes, COX-1 and COX-2. Further, as a COX-2 inhibitor, tolterodine can be further capable of inhibiting tumor cell growth by inhibiting the expression of the COX-2 enzyme.

The approach proposed in this application involves the use of tolterodine as an inhibitor of cyclooxygenase. Tolterodine is traditionally employed in the treatment of urinary incontinence and overactive bladder syndrome. Tolterodine acts by antagonizing muscarinic receptors. This new application of tolterodine is grounded in a unique perspective, that aside from its known pharmacological actions on muscarinic receptors, tolterodine may also exhibit inhibitory effects on the cyclooxygenase pathway.

The rationale behind considering tolterodine as a COX inhibitor stems from a detailed analysis of its molecular structure and the observation of its effects in preliminary studies. This analysis suggests that certain structural features of tolterodine may enable it to interact with the COX enzymes.

The inhibition of COX-1 and/or COX-2 by tolterodine allows it to serve as an anti-inflammatory agent to be used in the place of currently known NSAIDs, which are known to cause gastrointestinal problems such as stomach ulcers and bleeding and also heart-related side effects.

In this regard, the present subject matter relates to a method of inhibiting cyclooxygenase (COX) enzyme activity in a patient, including administering to a patient in need thereof a therapeutically effective amount of tolterodine.

The inhibitory effects of tolterodine on COX-1 and COX-2 were determined using COX inhibitor screening test kits, testing each compound's capacity to inhibit the conversion of arachidonic acid to prostaglandin. Tolterodine shows an $IC_{50}$ of about 4.53 µM for COX-1 and $IC_{50}$ of about 0.32 µM for COX-2. The $IC_{50}$ value serves as an indicator of a substance's potency in inhibiting biological functions, with a lower $IC_{50}$ denoting higher efficacy. The SI is a ratio of $IC_{50}$ values for COX-1 to COX-2. It indicates how selective a drug is towards inhibiting COX-2 over COX-1. A higher SI suggests greater selectivity for COX-2. The SI of Tolterodine is 14.3, which is considerably lower than celecoxib (a known COX-2 selective inhibitor) but higher than indomethacin and diclofenac.

In an embodiment, the present subject matter relates to a method of inhibiting cyclooxygenase (COX) enzyme activity in a patient, comprising administering to a patient in need thereof a therapeutically effective amount of tolterodine.

In another embodiment, the present subject matter relates to a method of reducing at least one of inflammation, fever, and pain in a patient, comprising administering to a patient in need thereof a therapeutically effective amount of tolterodine.

In another embodiment, the present subject matter relates to a method of inhibiting tumor growth in a patient, comprising administering to a patient in need thereof a therapeutically effective amount of tolterodine.

These and other features of the present subject matter will become readily apparent upon further review of the following specifications.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a method of inhibiting cyclooxygenase (COX) enzyme activity in a patient, comprising administering to a patient in need thereof a therapeutically effective amount of tolterodine.

In further embodiments, the present subject matter relates to a method of inhibiting cyclooxygenase (COX) enzyme activity in a patient, wherein the therapeutically effective amount of tolterodine is between about 0.005 μM and about 200 μM.

In some embodiments, the present subject matter relates to a method of inhibiting cyclooxygenase (COX) enzyme activity in a patient, wherein the COX enzyme is COX-1. In other embodiments, the present subject matter relates to a method of inhibiting cyclooxygenase (COX) enzyme activity in a patient, wherein the COX enzyme is COX-2.

In some embodiments, the present subject matter relates to a method of inhibiting cyclooxygenase (COX) enzyme activity in a patient, wherein the tolterodine has a moderate selectivity towards COX-2 over COX-1.

In further embodiments, the present subject matter relates to a method of inhibiting cyclooxygenase (COX) enzyme activity in a patient, wherein the administration of the tolterodine to the patient further reduces at least one of inflammation, fever, and pain in the patient.

In other embodiments, the present subject matter relates to a method of reducing at least one of inflammation, fever, and pain in a patient, comprising administering to a patient in need thereof a therapeutically effective amount of tolterodine.

In another embodiment, the present subject matter is directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises the present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for inflammation. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compound can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compound may also be administered as compositions prepared as foods for humans or animals, including medical foods, functional foods, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or similar formulations. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained-release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained-release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid, or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example, less than 10 microns.

The present compound has valuable pharmaceutical properties, which make it commercially utilizable. Accordingly, the present subject matter further relates to the use of the present compound for the treatment of inflammation and diseases associated with inflammation. Similarly, the present compound can be used to inhibit COX-1 and COX-2 enzyme activity in a patient. The present compound may also be used to treat pain and swelling associated with inflammation.

Accordingly, the inhibitory effects of tolterodine on COX-1 and COX-2 were determined using in vitro COX inhibitor screening test kits, testing each compound's capacity to inhibit the conversion of arachidonic acid to prostaglandin.

In another embodiment, a therapeutically effective amount of tolterodine is between about 0.005 µM and about 200 µM.

In a further embodiment, tolterodine shows an $IC_{50}$ value of about 4.53 µM for COX-1.

In yet another embodiment, tolterodine shows an $IC_{50}$ value of 0.32 µM for COX-2.

In an embodiment, tolterodine has a selectivity index for COX-1 over COX-2 of about 14.3.

The present subject matter further relates to a method of treating or preventing a disease comprising administering to a patient in need thereof a therapeutically effective amount of the compound herein.

In particular, the present subject matter relates to a method of treating one of the above-mentioned diseases or disorders comprising administering to a patient in need thereof a therapeutically effective amount of the compound herein.

In the above methods, the patient is preferably a mammal, more preferably a human. Furthermore, in the above methods, the present compound can be used. Similarly, the present compound can be used in combination therapy with one or more additional active agents.

The following examples relate to various methods of manufacturing certain specific compositions to conduct certain specific experiments as described herein.

Examples

An initial virtual screening of about 1400 FDA-approved drugs was conducted to identify candidate compounds with structures suitable for targeting the structure of COXs. Ultimately, tolterodine was chosen for further in vitro assessment for their inhibitory effects against COX-1 and COX-2.

Example 1

General Virtual Screening for Compounds Targeted at Inhibiting COX-1 and COX-2

The Schrodinger Maestro molecular modeling suite (Schrodinger LLC, New York, USA) was utilized for all stages of virtual screening modeling. QikProp software tools offer a fast, accurate, and user-friendly approach for predicting molecular characteristics. This software evaluates a given molecule's properties and compares them with those of substances present in 95% of commonly prescribed drugs. A series of graded filters is employed to identify potential interactions within the active site of the receptor and the ligand. This process involves constructing a grid with varying field sets that accurately score the ligand poses while simultaneously depicting the structure and attributes of the receptor. COX-1 and COX-2 inhibitor screening assay kits were obtained from Cayman Chemical (Ann Arbor, MI, USA).

Example 2

Identifying Tolterodine as a COX-2 Inhibitor

The COX-2 structure, with the PDB ID 5IKQ, was obtained from the Protein Data Bank website. This structure was then prepared using the Schrodinger Maestro software's protein preparation module, optimizing it for virtual screening and docking. This preparation involved removing crystallographic chemicals and water molecules, adding polar hydrogens to protonate the protein, and optimizing the structures using the OPLS2005 force field for energy minimization.

Docking grids were created using the Maestro grid-generating module, focusing on the defined ligand-binding areas in the structures. These grids encompassed a 20-nanometer area around the enzyme's active site.

A two-step docking approach was employed, beginning with standard precision docking (SP) and followed by extra precision docking (XP). This process utilized a Van der Waals radius scaling of 0.8. The extra precision docking is particularly aimed at reducing false-positive results. Compounds with high docking scores (less than −10) were selected for further analysis, examining their interaction with pocket residues and assessing their binding characteristics and how they occupied the pocket visually. The findings for tolterodine are detailed in Table 1.

TABLE 1

Docking Score of Tolterodine with Cox-2 (PDB: 5IKQ)

| Name | Docking Score (kcal/mol) | glide evdw | Glide Hbond | glide ligand efficiency |
|---|---|---|---|---|
| Tolterodine | −11.655 | −39.897 | −0.7 | −0.486 |

Virtual Screening and Docking

Table 1 presents a comprehensive analysis of the docking properties of Tolterodine with the COX-2 enzyme (PDB: 5IKQ). The primary findings include a docking score of −11.655 kcal/mol, indicating a strong binding affinity between Tolterodine and the enzyme. Further breakdown of the docking parameters reveals a significant van der Waals energy component (−39.897), a minor contribution from hydrogen bonding (−0.7), and an efficient ligand-protein interaction as denoted by the Glide Ligand Efficiency of −0.486. These results suggest that Tolterodine is a potent binder to COX2, underlining its therapeutic relevance.

Example 3

Enzyme (COXs) Inhibition Assay

The inhibitory effects of tolterodine on COX-1 and COX-2 were determined using COX inhibitor screening test kits, testing each compound's capacity to inhibit the conversion of arachidonic acid to prostaglandin. In test tubes, 25 mM Tris-HCl, pH 8.0, containing 5 mM EDTA, phenol, and 1 mM hematin was added. Tolterodine was dissolved in DMSO and added in concentrations ranging from 0.005-200 PM. Dimethyl sulfoxide alone was applied to control test containers. COX-1 or COX-2 enzymes were added to the test tubes, which were then preincubated for 10 minutes at 37° C. The arachidonic acid substrate was added, and the tubes were further incubated at 37° C. for 2 minutes. The compound's immunochemical assay was used to calculate the amount of prostaglandin produced.

Three separate experiments were used to calculate the IC50 values. The selectivity index was calculated as follows:

Selectivity Index (SI)=$IC_{50}$ COX-1/$IC_{50}$ COX-2

The results of these experiments are summarized in Table 2.

TABLE 2

Estimated IC50 Values (in µM) For Tolterodine Against COX-1 and COX-2. Celecoxib, indomethacin and diclofenac were control drugs

| Drug | COX-1 $IC_{50}$ (µM) | COX-2 $IC_{50}$ (µM) | SI |
|---|---|---|---|
| Celecoxib | 14.7 ± 1.045 | 0.045 ± 0.005 | 326.6 |
| Indomethacin | 0.1 ± 0.015 | 0.0725 ± 0.01 | 1.38 |
| Diclofenac | 0.05 ± 0.006 | 0.02 ± 0.001 | 2.5 |
| Tolterodine | 4.53 ± 0.12 | 0.32 ± 0.01 | 14.3 |

Cyclooxygenase Inhibition

Table 2 provides a comprehensive analysis of the inhibitory effects of various drugs on cyclooxygenase enzymes COX1 and COX2. Utilizing the IC50 values, measured in micromolar (M), the research evaluates the potency and selectivity of Tolterodine, compared with reference drugs like Celecoxib, Indomethacin and Diclofenac. The IC50 value serves as an indicator of a substance's potency in inhibiting biological functions, with a lower IC50 denoting higher efficacy. The SI is a ratio of IC50 values for COX1 to COX2.

SI indicates how selective a drug is towards inhibiting COX2 over COX1. A higher SI suggests greater selectivity for COX2. Tolterodine shows an IC50 of 4.53 µM for COX-1 and 0.32 µM for COX-2. The SI of Tolterodine is 14.3, which is considerably lower than celecoxib (a known COX-2 selective inhibitor) but higher than indomethacin and diclofenac. Tolterodine, with an SI of 14.3, suggests a moderate selectivity towards COX-2 over COX-1. This is significant because COX-2 selective drugs are often preferred for their reduced gastrointestinal side effects compared to non-selective COX inhibitors. In addition, large SI is also associated with cardiovascular side effects. Therefore, moderate selectivity of tolterodine is desirable.

It is to be understood that the method of inhibiting cyclooxygenase (COX) enzyme activity in a patient, comprising administering to a patient in need thereof a therapeutically effective amount of tolterodine is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting cyclooxygenase (COX) enzyme activity in a patient, comprising administering to a patient in need thereof a pharmaceutical composition consisting of a therapeutically effective amount of tolterodine as an active agent together with one or more pharmaceutically acceptable carriers, wherein no additional active agents are administered to the patient.

2. The method of inhibiting COX enzyme activity in a patient of claim 1, wherein the therapeutically effective amount of tolterodine is between about 0.005 µM and about 200 µM.

3. The method of inhibiting COX enzyme activity in a patient of claim 1, wherein the tolterodine is dissolved in dimethyl sulfoxide (DMSO).

4. The method of inhibiting COX enzyme activity in a patient of claim 1, wherein the COX enzyme is COX-1.

5. The method of inhibiting COX enzyme activity in a patient of claim 4, wherein the tolterodine shows an $IC_{50}$ value of about 4.53 µM for COX-1.

6. The method of inhibiting COX enzyme activity in a patient of claim 1, wherein the COX enzyme is COX-2.

7. The method of inhibiting COX enzyme activity in a patient of claim 6, wherein the tolterodine shows an $IC_{50}$ value of 0.32 µM for COX-2.

8. The method of inhibiting COX enzyme activity in a patient of claim 1, wherein the tolterodine has a selectivity index for COX-1 over COX-2 of about 14.3.

9. The method of inhibiting COX enzyme activity in a patient of claim 8, wherein the tolterodine has a moderate selectivity towards COX-2 over COX-1.

10. The method of inhibiting COX enzyme activity in a patient of claim 1, wherein the administration of the tolterodine to the patient further reduces at least one of inflammation, fever, and pain in the patient.

* * * * *